United States Patent [19]

Holub

[11] 4,119,709

[45] Oct. 10, 1978

[54] DIAGNOSTIC TEST

[76] Inventor: William R. Holub, 138 Shore Rd., Port Washington, N.Y. 11050

[21] Appl. No.: 658,818

[22] Filed: Feb. 17, 1976

[51] Int. Cl.$^2$ .................... G01N 33/16; A61K 43/00
[52] U.S. Cl. .................... 424/1; 23/230 B; 424/12
[58] Field of Search ............ 424/1, 1.5, 12; 195/103.5 R; 23/230 B, 230.6

[56] References Cited

U.S. PATENT DOCUMENTS

| | | | |
|---|---|---|---|
| 3,666,854 | 5/1972 | Eisentraut | 424/1 |
| 3,768,979 | 10/1973 | Mead et al. | 250/303 X |
| 3,775,615 | 11/1973 | Eisentraut | 23/230 B |
| 3,776,698 | 12/1973 | Eisentraut | 23/230 B |
| 3,901,654 | 8/1975 | Gross | 23/230 B |
| 3,960,492 | 6/1976 | Digiulio | 424/1 X |

FOREIGN PATENT DOCUMENTS 697,060  9/1953  United Kingdom ............ 23/230.6

OTHER PUBLICATIONS

Hemmaplardh et al., International Journal of Applied Radiation and Isotopes, vol. 27, No. 2, Feb. 1976, pp. 89–92.

*Primary Examiner*—Benjamin R. Padgett
*Assistant Examiner*—Christine M. Nucker
*Attorney, Agent, or Firm*—Jacobs & Jacobs

[57] ABSTRACT

A diagnostic test is provided based on competitive binding in which a partition coefficient is established for the substance whose concentration is to be determined and for the radioactive labeled form of the substance between liquid and solid phases.

10 Claims, No Drawings

DIAGNOSTIC TEST

The present invention relates to diagnostic tests based on competitive binding.

Competitive binding is a term used in the art to describe a diagnostic test in which an unknown substance and a radioactive (labeled) form of the substance compete for available sites on a suitable receptor. Upon separation of the materials that are bound to the receptor from those that are not bound, a count can be made of either the bound or unbound labeled substance, and the amount of unknown substance will be inversely related to the amount of bound labeled substance. Separation of bound from unbound material can be by means of ion exchange resins, but preferably a solid particulate inorganic sorbent is used, as proposed by U.S. Pat. No. 3,666,854. In this process, the inorganic sorbent is added to a sample fluid containing the unknown substance, the labeled substance and the receptor, and, after allowing the mixture to reach equilibrium, the resulting solution is centrifuged to separate the liquid phase from the solid phase.

U.S. Pat. No. 3,664,854 employs this procedure for determining the concentration of triiodothyronine using thyroid binding globulin as the receptor. According to U.S. Pat. No. 3,664,854, the liquid phase contains the hormone bound to the receptor and the solid phase contains the unbound hormone. This can be illustrated by equation (1) below, in which $$U = \text{unknown hormone}$$
$$L = \text{labeled hormone}$$
$$R = \text{receptor}$$
$$S = \text{sorbent}$$

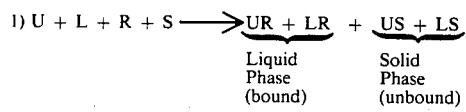

|  Liquid  | Solid |
|  Phase  | Phase |
|  (bound) | (unbound) |

In another procedure, a sequential addition is employed, and an equilibrium is not established. This can be demonstrated by equation (2):

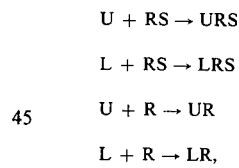

|  UR + LR | + | US + LS |
|  (Liquid |   | (Solid |
|  Phase)  |   | Phase) |

In both cases, the amount of unknown (U) will be a quadratic function of the ratio LR/LS. This can give rise to inaccuracies when determining the amount of the unknown from a curve plotting U as a function of LR/LS.

Furthermore, in cases where the sample fluid is blood serum or the like, wherein some of the unknown hormone is bound to binding proteins in the serum, the prior art has proposed to separate the unknown hormone from the binding protein before contact with the sorbent, such as by denaturing and centrifugation, and the thus separated hormone is contacted with labeled hormone, receptor and sorbent. Clearly, this additional step can be time consuming and can also give rise to analytical inaccuracies.

There is thus a need for a method of competitive binding diagnostic testing that will be both simpler to carry out and more accurate in results.

It is therefore an object of this invention to simplify the manipulative steps of a competitive binding diagnostic test, and to make the test more accurate.

This and other objects of the invention are fulfilled by the present invention, which provides a method of determining the concentration of a substance in a sample fluid by competitive binding, which comprises forming an admixture of a predetermined amount of said sample fluid, a predetermined amount of a radioactive isotope labeled form of said substance, a predetermined amount of a receptor or binding agent for the labeled and unlabeled forms of the substance, and a predetermined amount of a particulate sorbent coated with the receptor for the labeled and unlabeled forms of the substance, allowing the resulting heterogenous liquid phase/solid phase system to equilibrate, said liquid phase comprising said substance bound to the binding agent and said radioactive isotope bound to the binding agent and said solid phase comprising said coated sorbent to which is bound said substance and said radioactive isotope, separating the liquid phase from the solid phase after equilibration, and counting with a radiation counter the radioactivity of the liquid phase or the solid phase.

In contrast to the prior art systems that relied on separation of bound from unbound forms of the labeled hormone or other unknown, the present invention is based on establishing a partition coefficient for the sorbent between a liquid and a solid phase. This can be diagrammatically illustrated by equation (3) below:

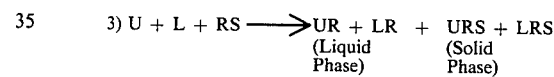

|  | (Liquid | (Solid |
|  | Phase) | Phase) |

Equation (3) actually represents four simultaneous reactions:

$$U + RS \rightarrow URS$$

$$L + RS \rightarrow LRS$$

$$U + R \rightarrow UR$$

$$L + R \rightarrow LR,$$

which establish a partition coefficient:

$$K = LRS/LR.$$

Since the concentration of U is proportional to the concentration of LRS, and since the number of radioactive counts is also directly proportional to the concentration of LRS, it is possible to obtain a direct linear relationship between the concentration of the unknown, U, and the total radioactive counts. However, this relationship will only be true if a mass equilibrium is established and if the partition coefficient, K, is kept constant. This is accomplished by establishing a mass equilibrium using a receptor (R) adsorbed on a suitable solid adsorbent (S) for the solid phase and by providing the receptor (R) in the liquid phase as well. The partition coefficient is kept constant by fixing the concentration of receptor (R) on the adsorbent and in the liquid phase, the solid adsorbent (S) and the radioactive labeled molecule (L), whereby the amount of radioactivity detected in the solid phase is directly linearly proportional to the concentration of the unlabeled (endogenous) molecule in the sample added. Whereas the prior art systems relied on a separation of labeled substance bound to the receptor from unbound labeled substance, the present invention involves simply an establishment of a partition of the receptor between two phases, i.e. solid and liquid. One important feature in accomplishing this result is the use of an adsorbent (S) that has been precoated with a sufficient amount of the receptor (R) so that any binding agents in the test sample can be ignored, and hence there is no need for a prior extraction of such binding agent.

The solid adsorbent used in the present invention may be any solid organic or inorganic particulate material that is able to adsorb the receptor (R). Suitable adsorbents are well known in the art, and reference is made to U.S. Pats. Nos. 3,666,854 and 3,721,528 for a disclosure of operable adsorbents. In particular, kaolin, sucrose, starch, sodium carbonate, calcium carbonate, calcium phosphate, magnesium carbonate, calcium oxide, silicic acid, magnesium silicates, charcoal, magnesium oxide, aluminum oxide and fuller's earth are suitable adsorbents. Preferably, the adsorbent is kaolin (china clay), porcelain clay, hydrated aluminum silicate, $H_2Al_2Si_2O_8 \cdot H_2O$ approx.), due to its combination of large surface area, good suspension properties, solid adhesion, fine particle size, availability and ease of handling. Before use, the kaolin is washed with acid, e.g. a mineral acid, to remove impurities.

For use in the present invention, the sorbent (S) is precoated with an amount of receptor (R) that will be at least sufficient to bind all of the labeled substance (L) to be used in the test. This will insure that there will be sufficient sites on the receptor (R) to bind labeled and unlabeled forms of the test material. This can be determined empirically by adding larger amounts of the receptor (R) to the sorbent (S) until the uptake of a given amount of labeled material becomes constant. Furthermore, there must be an additional amount of the receptor in the liquid phase so as to establish the partition coefficient. This amount will not be critical, and generally can be of the same amount as used in the precoating of the sorbent. If desired, the sorbent (S) may be coated with the receptor (R) before use in the test. Alternatively, the sorbent (S) can be coated with the receptor (R) during the test by mixing the sorbent (S) with an amount of receptor (R) sufficient to coat the sorbent (S) and to provide receptor (R) in the liquid phase.

In operation, measured amounts of a) the sorbent (S) that has been precoated with the receptor or binding agent (R), b) the sample fluid containing an unknown amount of the substance (U) under investigation, and c) the radioactive labeled form (L) of the substance are mixed together, the mixture also containing receptor (R) in the liquid phase thereof. Alternatively, measured amounts of the receptor (R) and the sorbent (S) are admixed, after or during which time the sample fluid is added, and then the radioactive material (L) is admixed to form the final mixture. In either case, the final mixture is allowed to stand for a short period of time, e.g. from about 10 to about 30 minutes, preferably from about 15 to about 20 minutes, to permit the mass equilibrium to be established. Then the resulting solid and liquid phases are separated, as by centrifugation, and the radioactivity of the solid or liquid phase is counted. The amount of the test substance (U) is determined from previously prepared standard curves plotting concentration of the test compound against the radioactive counts per minute of the solid or liquid phase, respectively.

The diagnostic test of the invention is neither time nor temperature dependent. Thus, once the mass equilibrium is established, no adverse effects are noted at longer contact times, i.e. contact time exceeding 30 minutes. Similarly, ambient temperature, i.e. about 65° to about 85° F., can be used without any special cooling or heating.

The present invention can be used in the determination of the concentration of any biologically active substance, using a receptor (R) that will readily selectively bind the molecule and its radioactive labeled form. For example, the following triads may be used:

| Test Molecule | Labeled Molecule | Receptor |
|---|---|---|
| Triiodothyronine ($T_3$) | $T_3I^{125}$ | $T_3$-antibody |
| Fe | $Fe^{59}$ | Transferrin |
| Pituitary hormone (TSH) | $TSH-I^{125}$ | TSH-antibody |
| Digoxin | 3-o-succinyl digoxigen-$I^{125}$ tyrosine | Digoxin antibody |
| Vitamin $B_{12}$ | $CO^{57}$-cyanocobalamin | Vitamin $B_{12}$-antibody |

The present invention is illustrated by the following Examples. In this specification and the appended claims, all parts and proportions are by weight, unless otherwise noted.

EXAMPLE 1

The following reagents were prepared for determination of L-thyroxine ($T_4$) in blood.

| Reagent | Description |
|---|---|
| 1. | Pooled Serum. Blood obtained from humans containing $T_4$ and thyroid binding globulin (TBG). |
| 2. | Kaolin Suspension. Suspend 180g of acid washed kaolin (No. K-5, Fisher Scientific Co., Springfield, N.J.) in 1000 ml of dilute sulfuric acid (0.036 N, 1.0 ml concentrated acid to 1000 ml water, adjust pH to 2.0 ± 0.2) and add 50 ml pooled serum. |
| 3. | $I^{125}$thyroxine-protein solution (20 mcg/dl). To 800 ml barbital buffer (0.075 mol/liter) add 15.0 ml pooled serum, 8.0 mixing propylene glycol, 1.0g sodium azide and 0.40 ml of $I^{125}$thyroxine (activity 321 uCi/ml; Abbott Laboratories, North Chicago, Ill.). Dilute to 1000 ml with water, mix well. |
| 4. | Phosphate Buffer. Dissolve 13.92g of potassium phosphate, dibasic ($K_2HPO_4$), 2.76g of sodium phosphate, monobasic, hydrate ($NaH_2PO_4 \cdot H_2O$), and 8.76g of NaCl in about 900 ml of water. Adjust pH to 7.6 ± 0.1 with phosphoric acid (33 mmol/liter) or KOH (0.1 mol/liter). Dilute to 1000 ml with water and mix. |
| 5. | Standard Diluent. Dilute 100 ml of reagent No. 4 with 800 ml of water. Add 7.9g of NaCl and 60g of bovine albumin (plasma fraction five). Adjust pH to 7.4 ± 0.2 with phosphoric acid or KOH. Dilute to 1000 ml with water. Stable for at least three months at 4° C. |
| 6. | Thyroxine Stock Standard (1 mg/ml). Add 18.6 mg of L-thyroxine (Na salt, pentahydrate: Sigma Chemical Co., St. Louis, Mo.) and 2.5 ml of propylene glycol to a 25 ml volumetric flask. Dissolve by adding NaOH (0.1 mol/liter) in 2 ml fractions with mixing until solution is clear. Dilute to volume with water and mix. Transfer 2.5 ml aliquots to screw capped tubes and store frozen. Stable for six months. |
| 7. | Thyroxine Dilute Stock Standard (100 ug/dl). Dilute 0.1 ml reagent No. 6 to 100 ml with reagent No. 5 in amounts to give samples having a $T_4$ concentration of 2, 6, 10 and 14 ug/dl. A sample with zero $T_4$ is obtained by using only reagent No. 5 |

A thyroxine radioassay was carried out as follows:
STEP 1. PIPETTE

Add exactly 0.05 ml (50 ul) of the patient's serum containing $T_4$ and TBG directly into 1.0 ml of reagent 2 in a sample tube.

STEP 2.  MIX & INCUBATE
Cap and mix or vortex well. Allow to stand undisturbed for 5 minutes.

STEP 3.  DISPENSE
Dispense exactly 2.0 ml of reagent 3 to the sample tube.

STEP 4.  MIX & INCUBATE
Recap the tube and mix or vortex well. Allow tube to stand undisturbed for a minimum period of 15 minutes at room temperature.

STEP 5.  CENTRIFUGE
Centrifuge the tube for 2-3 minutes at 1800-2600 rpm.

STEP 6.  DECANT
Completely decant and discard supernatant and shake out most of the remaining liquid (or leave tube inverted against a paper towel).

STEP 7.  COUNT
Place tube containing the solid material into a gamma counter and count for one-half minute or sufficient time to accumulate 20,000 to 30,000 counts per minute (cpm).

STEP 8.  CALCULATE
Determine the concentration of $T_4$ in patient's serum by reading the value of $T_4$ (ug/dl), as the ordinate, corresponding to the cpm obtained, as the abscissae, on the "standard curve".

The "standard curve" was prepared by following the radioassay procedure described above, except that reagent No. 7, at $T_4$ concentrations of 0, 2, 6, 10 and 14 ug/dl, is substituted for the patient's serum. A standard curve is obtained by plotting $T_4$ concentration (ug/dl) as ordinate vs. cpm as abscissae. In preparing the standard curve, an assay recovery of $T_4$ ranged from 91–102% over the range of 2–14 ug/dl. Correlation coefficient with a reference Murphy-Pattee CPB method, $r = 0.892$. Correlation coefficient with a RIA thyroxine radioimmunoassay method, $r = 1.124$.

The test procedure was carried out on hypo-, hyper- and euthyroid samples ($n = 60$) using a single operator and with several operators with the following results:

| | Mean Concentration of $T_4$* (ug/dl) | | |
|---|---|---|---|
| | Hypothyroid | Normal | Hyperthyroid |
| Single Operator | 2.7 ± 0.5 | 7.2 ± 0.7 | 17.3 ± 1.5 |
| Several Operators | 2.5 ± 0.7 | 7.4 ± 1.5 | 17.6 ± 2.0 |

*plus or minus two standard deviations.

It is noted that the test procedure does not involve any step of extracting the TBG in the patient's sample. This amount of TBG can be ignored in view of the very large amounts of TBG provided on the kaolin and in reagent No. 3. This is an important feature of the present invention.

EXAMPLE 2

The amount of receptor for use in a $T_4$ diagnostic test was determined as follows using $T_4$-Antibody as the receptor:

| Reagent | Description |
|---|---|
| 8. | $T_4$-Antibody. Reconstitute lyophilized $T_4$-Antibody with Reagent 8 to the desired volume. Note that a "unit dose" of $T_4$-Antibody is defined as the amount binding 80% of 700 pg of $T_4$-$I^{125}$, and equals 100 μl. |
| 9. | $I^{125}$Thyroxine Solution. $I^{125}$thyroxine (see Reagent 3) was diluted with sufficient 0.075 molar barbital buffer to a "standard volume" providing 40,000 cpm. |

To 0.05 ml aliquots of reagent 2 were added from 50 to 300 μl of reagent 8. After 15 minutes the "standard volume" of reagent 9 was added to each aliquot, the mixture shaken, and allowed to stand for 20 minutes. The material was centrifuged, separated into liquid and solid phases and the solid phase counted to determine the percent uptake of the $I^{125}$ thyroxine by the precoated kaolin. The results were as follows:

| μl of Reagent 8 Added | $I^{125}$ Thyroxine Bound By Precoated Kaolin (Per Cent) |
|---|---|
| 0 | 8 |
| 50 | 37 |
| 100 | 50 |
| 200 | 72 |
| 300 | 91 |

Addition of unlabeled thyroxine standards to the mixture before centrifugation displaced an amount of labeled thyroxine in relation to the molar concentration of unlabeled thyroxine added. From these data, a test procedure for determination of $T_4$ based on the procedure is employed using 25 μl of reagent 1, 100 μl of reagent 3, 300 μl of reagent 8 and 1 ml of a kaolin suspension prepared by diluting one volume of reagent 2 diluted with 5 volumes of a barbital buffer to give a pH of 8.6. In this procedure, the solid phase is counted.

EXAMPLE 3

Table I below lists the reagents and amounts thereof for carrying out four additional diagnostic tests at room temperature. In each case, the binder (S), receptor (R) and unknown (U) are admixed well and then allowed to stand for about 15 minutes to insure full coating of the sorbent with the receptor. The labeled molecule (L) is then added to the mixture and mixed well and then allowed to stand again, this time to establish the partition coefficient. Table I reports the time to establish the partition coefficient as the "incubation time". After the incubation time, the sample is centrifuged, the liquid discarded and the remaining solid is counted for radioactivity. Table I reports the amount of labeled material bound by the receptor in the solid phase, which is an indication of the efficiency of the system.

TABLE I

| Unknown (U) | | Labeled Molecule (L) | Receptor (R) | Binder (S) | Amount of L Bound By R (%) | Incubation Time (min.) |
|---|---|---|---|---|---|---|
| Identity | Reagent | | | | | |
| Fe | 100 μl of patient's serum | 100 μl of $Fe^{59}Cl$ in 0.1N HCl | 100 μl of reagent 1. Reagent 1 | 1 ml of reagent 2 after | 92–99 | 10 |

TABLE I-continued

| Unknown (U) | Labeled Molecule (L) | Receptor (R) | Binder (S) | Amount of L Bound By R (%) | Incubation Time (min.) |
|---|---|---|---|---|---|
| | (Amersham-Searle) | contains Transferrin used as the receptor. | admixture with barbital buffer to pH 8.6 | | |
| Thyroid stimulating hormone (TSH) | 100 μl of patient's serum | 100 μl of TSH-I$^{125}$ (100 μCi) (Cambridge Nuclear) | 200 μl of TSH-Antibody (rabbit) Calbiochem 869007 | 1 ml of reagent 2 after dilution 1:5 with reagent 4 | 77-85 | 30 |
| Digoxin | 100 μl of patient's serum | 100 μl of 3-o-succinyl digoxigenin-I$^{125}$ tyrosine (Corning No. No. 474030) | 100 μl of Digoxin Antibody Calbiochem 869059 diluted 1:50 with reagent 4 | 1 ml of reagent 2 after dilution 1:20 with reagent 4 | 70-82 | 20 |
| Vitamin B-12 | 200 μl of patient's serum | 100 μl of Co$^{57}$-cyanocobalamin (70-200 μCi/mg) (Amersham-Searle) | 100 μl of Intrinsic Factor, RIA Products RP-1506 diluted 1:10 with reagent 4 | 1 ml of reagent 2 after dilution 1:3 with 1:3 with reagent 4 | 85-92 | 45 |

What is claimed is:

1. A method of determining the concentration of a substance in a sample fluid by competitive binding, which comprises forming an admixture of a predetermined amount of said sample fluid, a predetermined amount of a radioactive isotope labeled form of said substance, a predetermined amount of a receptor capable of binding the labeled and unlabeled forms of the substance, and a predetermined amount of a particulate solid sorbent coated with a further amount of said receptor, said sorbent being precoated, before said admixture is formed, with said further amount of receptor, said further amount being at least sufficient to bind all of the labeled substance, allowing the resulting heterogenous liquid phase/solid phase system to equilibrate, said liquid phase comprising said substance bound to the receptor and said radioactive isotype bound to the receptor and said solid phase comprising said coated sorbent to which is bound said substance and said radioactive isotope, separating the liquid phase from the solid phase after equilibration, and counting with a radiation counter the radioactivity of the liquid phase or the solid phase.

2. The method according to claim 1, wherein said solid sorbent is selected from the group consisting of kaolin, surcrose, starch, sodium carbonate, calcium carbonate, calcium phosphate, magnesium carbonate, calcium oxide, silicic acid, magnesium silicates, charcoal, magnesium oxide, aluminum oxide and fuller's earth.

3. The method according to claim 1, wherein said solid sorbent is kaolin.

4. The method according to claim 3, wherein the substance is L-thyroxine ($T_4$), the labeled form of the substance is $T_4$-I$^{125}$, and the receptor is thyroid binding globulin.

5. The method according to claim 3, wherein the substance is L-thyroxine ($T_4$), the labeled form of the substance is $T_4$-$^{125}$, and the receptor is $T_4$-antibody.

6. The method according to claim 3, wherein the substance is triiodothyronine ($T_3$), the labeled form of the substance is $T_3$-I$^{125}$, and the receptor is $T_3$-antibody.

7. The method according to claim 3, wherein the substance is Fe, the labeled form of the substance is Fe$^{59}$, and the receptor is Transferrin.

8. The method according to claim 3, wherein the substance is thyroid stimulating hormone (TSH), the labeled form of the substance is TSH-I$^{125}$, and the receptor is TSH-antibody.

9. The method according to claim 3, wherein the substance is digoxin, the labeled form of the substance is 3-o-succinyl digoxigen-I$^{125}$ tyrosine, and the receptor is digoxin antibody.

10. The method according to claim 3, wherein the substance is vitamin $B_{12}$, the labeled form of the substance is CO$^{57}$-cyanocobalamin, and the receptor is vitamin $B_{12}$-antibody.